US007244902B2

(12) United States Patent
Popp et al.

(10) Patent No.: US 7,244,902 B2
(45) Date of Patent: Jul. 17, 2007

(54) METHOD FOR CLASSIFYING WINE AND COFFEE

(75) Inventors: Michael A. Popp, Neumarkt (DE);
Günther Bonn, Innsbruck (AT);
Christian Huck, Innsbruck (AT);
Wolfgang Guggenbichler, Innsbruck (AT)

(73) Assignee: Bionorica AG, Neumarkt (DE)

( * ) Notice: Subject to any disclaimer, the term of this patent is extended or adjusted under 35 U.S.C. 154(b) by 455 days.

(21) Appl. No.: 10/479,064

(22) PCT Filed: May 6, 2002

(86) PCT No.: PCT/EP02/04988

§ 371 (c)(1),
(2), (4) Date: May 28, 2004

(87) PCT Pub. No.: WO02/097431

PCT Pub. Date: Dec. 5, 2002

(65) Prior Publication Data

US 2004/0222136 A1    Nov. 11, 2004

(30) Foreign Application Priority Data

May 28, 2001    (DE)    ............................... 101 24 917

(51) Int. Cl.
*B07C 5/00*    (2006.01)
(52) U.S. Cl. ...................... 209/577; 209/588; 250/910
(58) Field of Classification Search ................ 250/910; 209/552, 559, 576, 577, 587, 588
See application file for complete search history.

(56) References Cited

U.S. PATENT DOCUMENTS 4,490,042 A * 12/1984 Wyatt ........................ 356/340

(Continued)

FOREIGN PATENT DOCUMENTS

DE          695 01 333 T2      5/1994

(Continued)

OTHER PUBLICATIONS

S.J. Haswell & A.D. Walmsley, "Multivariate Data Visualisation Methods Based in Multi-Elemental Analysis of Wines and Coffees Using Total Reflection X-Ray Fluorescence Analysis"; Journal of Analytical Atomic Spectrometry; Feb. 1998; vol. 13; pp. 131-134.

(Continued)

*Primary Examiner*—Patrick Mackey
*Assistant Examiner*—Mark Hageman
(74) *Attorney, Agent, or Firm*—Akerman Senterfitt

(57) ABSTRACT

A method for classifying beverages of natural origin, such as wine or coffee. Classification is carried out by means of NIR spectroscopy and corresponding numerical-mathematical conditioning of the spectral data of the individual beverage samples, wherein respective obtained spectra are then correlated with a predetermined beverage, class. By means of the method of the invention it is possible to classify wines by sort of wine, growing regions, grape, vine, vintage, kind of material or wood of the wine cask used, and varying degree of maturity of the wine, and by other chemical parameters. Coffee, for example, may be classified by coffee sort, country of origin, coffee growing region, roasting method and defined chemical parameters, e.g., caffeine content, or chlorogenic acid content.

20 Claims, 7 Drawing Sheets

**Cluster imaging: maturing process
(Tempranillo and Cabernet Sauvignon)**

U.S. PATENT DOCUMENTS

| | | | | |
|---|---|---|---|---|
| 5,034,609 A | * | 7/1991 | Satake et al. | 250/339.11 |
| 5,453,619 A | * | 9/1995 | Asselain et al. | 250/339.12 |
| 5,475,612 A | | 12/1995 | Espinosa et al. | |
| 5,680,321 A | | 10/1997 | Helmer et al. | |
| 5,753,511 A | | 5/1998 | Selinfreund | |
| 5,818,045 A | * | 10/1998 | Mark et al. | 250/339.12 |
| 6,087,182 A | | 7/2000 | Jeng et al. | |
| 6,232,124 B1 | | 5/2001 | Selinfreund | |
| 6,885,003 B1 | * | 4/2005 | Dubernet | 250/339.09 |
| 2005/0065732 A1 | * | 3/2005 | Tilton et al. | 702/19 |

FOREIGN PATENT DOCUMENTS

| | | |
|---|---|---|
| DE | 198 30 720 C1 | 1/2000 |
| EP | 0 393 459 A1 | 10/1990 |
| FR | 2 797 688 | 2/2001 |
| WO | WO 89/09931 | 10/1989 |
| WO | WO 00/17611 | 3/2000 |
| WO | WO 00/64242 | 11/2000 |

OTHER PUBLICATIONS

L. E. Rodriguez-Saona, F. S. Fry, M.A. McLaughlin, E.M. Calvey, "Rapid Analysis of Sugars in Fruit Juices by FT-NIR Spectroscopy"; Journal of Analytical Atomic Spectrometry; 2001; vol. 336; Abstract.

Sivakesava, S. and Irudayaraj, J. "Determination of Sugars in Aqueous Mixtures Using Mid-Infared Spectroscopy"; Journal of Analytical Atomic Spectrometry; Sep. 2000; vol. 16; Abstract.

* cited by examiner

1. Chianti, Lagrein

2. Chianti, Lagrein

1. Chianti, Lagrein, Cabernet

2.Chianti, Lagrein, Cabernet

3. Chianti, Lagrein, Cabernet

Cabernet, 1997 and 1998 vintages

Cluster imaging: maturing process (Tempranillo and Cabernet Sauvignon)

METHOD FOR CLASSIFYING WINE AND COFFEE

CROSS REFERENCE TO RELATED APPLICATION

This application is a national stage of PCT/EP02/04988 filed May 6, 2002 and based upon DE 101 24 917.9-52 filed May 28, 2001 under the International Convention.

FIELD OF THE INVENTION

The present invention relates to a method for classifying beverages of natural origin. The invention in particular serves for the classification of wine and coffee.

BACKGROUND OF THE INVENTION

The classification of wines, e.g., according to sort of wine, growing region, grape, and vintage, is at present only possible by the sensory subjective way through the excellently trained sense of smell and taste of a wine connoisseur. Besides the inaccuracies inherent in nature such as, e.g., in the differentiation of single vintages of a wine, these sensory qualities are limited to only a relatively small number of persons.

Accordingly attempts have not been scarce to examine the various wines by scientific methods, for instance the analysis of single chemical parameters such as sugar content, acidity, ethanol content etc., and/or by physico-chemical methods such as optical rotary dispersion, index of refraction etc., and achieve a classification as named at the outset through interpretation of the single data, a group of data, or the entirety of such data.

Owing to the complex composition of the wine on the one hand, but on the other hand the similarity of single parameters, any attempts at giving a reliable statement with the aid of analytical methods, e.g. about sort of wine, growing region, grape and vintage of a wine in question, have failed up to the present.

However, for various reasons it is sensible to have at one's disposal a reliable method for classifying wines. For one thing, monitoring trade products in terms of food technology and their conformity with statutory requirements is hereby possible, for it is possible to detect, e.g., whether the criteria of designation of the growing region are complied with, such as, e.g., whether or not an inadmissible blending with another grape/growing location exists. On the other hand, monitoring the production process and maturation in storage in the course of wine production by the wine grower would be conceivable with such a classification system.

Apart from the above mentioned classical prior art of wine analytics it is moreover known from the graduation thesis entitled, "Anwendung multivariater Methoden und kunstlicher neuronaler Netze zur Klassifizierung von Spirituosen mittels Headspace-GC/MS-Kopplung", presented by Patrick Kursawe, Chair for Analytical Chemistry of Ruhr-Universitat Bochum 1998, to classify various spirits ranging from grappa to rum, with relative reliability by applying multivariate methods and artificial neuronal networks and principal components analysis.

With regard to classification of wine by the modern chemometrical methods, Montanarella et al. (Montanarella, T., Bassani, M. R., Broas, O. (1995): Chemometric Classification of Some European Wines Using Pyrolysis Mass Spectrometry, Rapid Comm. Mass Spectrom. 9 (15), 1589-1593] have attempted, by utilizing various multivariate methods as well as backpropagation networks, to classify wines with regard to their country of origin with the aid of pyrolysiso mass spectra. A fine differentiation between different regions did, however, fail.

SUMMARY OF THE INVENTION

Starting out from the prior art of Montanarella et al. (1995) it is therefore an object of the present invention to furnish a reliable method for classifying beverages of natural origin, in particular wines and coffees according to—besides the visually recognizable color—at least wines and coffees, respectively.

In particular, the method of the invention for classifying beverages of natural origin includes the following steps:

a) providing a plurality of beverage classes, with a plurality of calibration beverage samples per class each, having a plurality of known class properties;

b) irradiating measurement light from a predetermined wavelength range into the beverage samples;

c) detecting the measurement light passed through, reflected, re-emitted, and/or dispersed from, the beverage samples;

d) determining the wavelength-dependent ratio of irradiated to detected measurement light (spectrum) for each beverage sample of a class;

e) performing numerical-mathematical conditioning of the spectral data of the individual beverage samples;

f) correlating the spectra of a plurality of beverage samples with a predetermined beverage class;

g) compiling a database from the conditioned spectral data with different beverage classes based on the measured beverage samples of the individual classes for calibration of a class correlation;

h) repeating at least once the steps b) to e) with at least one beverage sample having at least partly unknown properties; and i) determining the beverage classes to which the unknown beverage sample is to be associated, with the aid of a class correlation of the measured spectra, by using the compiled calibration database of step g).

In a particularly preferred manner, wine and coffee are used as a beverage.

BRIEF DESCRIPTION OF THE FIGURES

Further advantages and features of the present invention result from the description of embodiments and by reference to the drawings, wherein.

DETAILED DESCRIPTION

Figure 1:
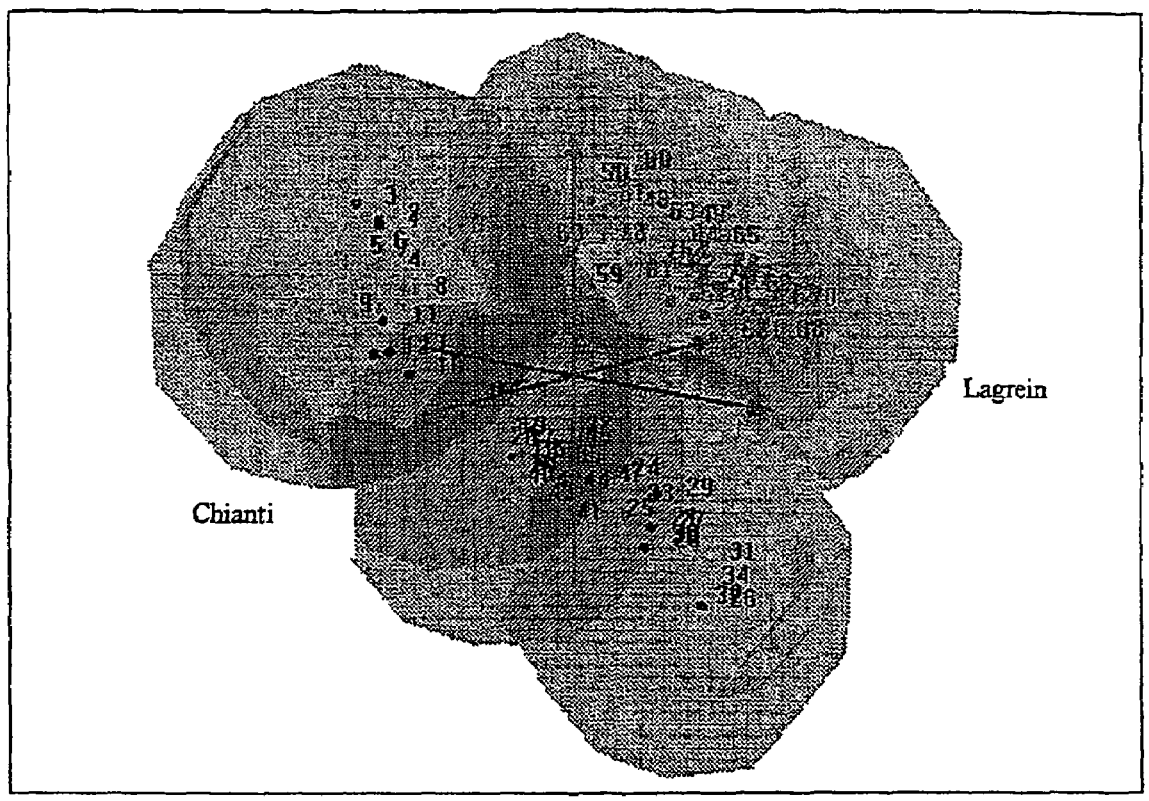
FIG. 1 shows a first cluster representation of the wine sorts: Chianti and Lagrein.

By the method of the invention it is possible for the first time to classify a wine sample at least with regard to its associated sort of wine (besides the visually detectable color). As a rule, however, even classifications according to grape, growing region and vintage are possible.

The expression "class" or "wine class" is understood, for the purposes of the present invention, as a group of wines having defined properties, i.e. class properties, such as, e.g., sort of wine, grape, growing region and vintage.

Thus, for instance, the wine class "Chianti Antinori 1996" may exhibit the class properties: sort of wine: "red wine, Chianti type", "grape: main constituent: Sangiovese", growing region: "South Tyrol", and vintage "1996."

By the method of the invention it was possible by way of example to achieve an unambiguous classification with unknown wine samples for the following wines:
Pure wines: Lagrein and Cabernet: 1997 and 1998 vintages, Laimburg Wine Research Center (Weinforschungszentrum Laimburg); and
Chianti Classico Villa Antinori: 1996 vintage, growing regions Tyrol and South Tyrol, grape: main constituent: Sangiovese.

Moreover it was surprisingly found that the method of the invention is also particularly well suited for the classification of coffee in accordance with the classes: coffee sort; country of origin, coffee growing region; roasting method; chemical parameters, in particular caffeine content, bittering content, acidity, in particular content of chlorogenic acids, toxicological parameters, in particular content of herbicides and pesticides.

In accordance with the present invention it is preferred to record an NIR spectrum of the wines in question without any further preparation of samples.

For this purpose, e.g., a commercially available NIR-VIS spectrometer may be used. Numerical-mathematical conditioning of the spectral raw data may be carried out with an equally commercially available software, e.g. BCAP V 6.00 [BOHLER AG, ANATEC, CH-9240 Uzwil, Switzerland].

Class correlation may also be performed with a commercially available software, such as Nircal 3.0 [Buchi AG, CH-9230 Flawil1], e.g., through principal components analysis and clustering. The result may be represented, for example, in the form of a cluster representation as a 3-D plot, wherein the axes represent the principal components.

In order to calibrate the method of the invention, initially of a plurality of wine samples known with regard to sort of wine, grape or grapes, growing region and vintage (as a rule at least 10 samples/class property) one respective NIR spectrum is measured, as a rule repeatedly, in order to buffer statistical variations. This data is as a rule conditioned numerically-mathematically in order to reduce the bulk of data and concentrate on the essential characteristics of the spectra.

Then the method is correlated with these samples such that multivariate methods like principal components analysis, clustering, artificial neuronal networks, are applied to this conditioned data, to be able to state based on the abundant data whether or not an unknown wine sample, when also measured by NIR spectroscopy, belongs to this class.

Multivariate methods refer to evaluation methods utilizing more than just one measurement signal of a same sample in order to arrive at an analysis result. Among these methods there are i.a. Multi-linear Regression (MLR), Principal Components Analysis (PCA), Principal Components Regression (PCR), the method of Partial Least Squares (PLS), clustering methods, and artificial neuronal networks.

For the artificial neuronal networks in particular the following algorithms may be considered: backpropagation networks, Dynamic Learning Vector Quantization (DLVQ algorithm), Radial Basis Functions (RBF networks), in particular RBF networks (RBF-DDA networks) trained with the Dynamic Decay Adjustment algorithm (DDA algorithm).

PCA performs a separation of the original data matrix into two matrices, referred to as factor values and loadings. In the original data space a vector is selected in such a way that a maximum possible part of the variance is imaged when projecting the data onto it. This vector is the first principal component. A second principal component is orthogonal to the first principal component, and optionally a third principal component is orthogonal to the first and second principal components, wherein the second and third principal components are to image as much as possible of the variance not described yet by the first and second principal components, respectively.

The coordinates along the first principal component contain the essential information of the data, with the second and third principal components essentially reflecting scattering.

This process is repeated until either the number of the principal components corresponds to that of the dimension of the starting data, or until a particular termination criterion is reached.

The principal components thus obtained are linear combinations of the original dimensions. They are linearly independent of each other, so that a defined number of principal components contain less redundant information than the same number of starting variables.

Moreover the thus-obtained principal components each describe a maximum possible variance of the starting data not described yet by the already existing principal components. As a result, generally the first three to five principal components reflect the essential proportion of the information in the set of data.

Mathematically speaking, principal components analysis is a characteristic value problem, the fundamental solution of which is known to the person having skill in the art.

The result of principal components analysis also is a transformation of the N-dimensional original data space, with the result that the first dimensions contain the essential data portions strongly contributing to the overall variance, and the last dimensions basically reflecting no more than the noise content. In this way the structure of the spectroscopic data in question may be represented by plotting the first principal components relative to each other. As a two-dimensional, preferably 3-D, image they are then available for visual evaluation to the user who is left with the option of selecting a representation that enables a classification of wine samples into particular classes and which may, of course, also be automated.

In calibration, the so-called tolerance circles of the images may then be selected so as to be adaptable to particular classes, where necessary, in order to facilitate classification.

Preferably about 70% of the totality of wine samples measured per class are used for calibration, and about 30% for validation of the method of the invention.

For better reproducibility of the method of the invention, the samples are measured at a constant temperature, preferably at approximately 23° C.

The method of the invention allows classification of wine samples with the following class properties, wherein the following group is encompassed at least in part: sort of wine; growing region; grape; vine; vintage; kind of material, in particular species of wood of the wine cask used for storage/maturing, preferably kind of oak, e.g., American oak, French oak or also Hungarian oak; varying maturity degree of storage in the cask; chemical parameters, in particular ethanol content, sugar content, acidity, 802 content; tannin content; pH; water content; dry residue; polyphenol content; toxicological parameters, in particular glycol content and/or methanol content.

Further preferred embodiments are within the scope of the present invention.

In FIGS. 1 to 6, cluster representations for different wines and vintages are shown.

Initially NIR spectra of various wines were established. These spectra were processed in 20-ml measuring cuvettes in the absence of any further sample preparation, with an NIR-VIS spectrometer (FT-IR universal spectrometer) and with the BCAP V6.0 software (BOHLER Analytical Package, BOHLER AG, Anatec; CH-9240 Uzwil, Switzerland).

Classification through principal components analysis/clustering was performed with the aid of the NIRCAL 3.0 software (BUHLER AG, Anatec; CH-9240 Uzwil, Switzerland). This was a software for controlling the NIR-VIS spectrometer and chemometrical evaluation of the recorded spectra.

The optical layer thicknesses for measurement of the spectra in the examples were 0.5 mm or 3 mm.

All of the samples were measured at a constant thermostated temperature of approx. 23° C.

The exemplarily examined wines were distributed among three different wine classes:

1. Pure wines, i.e., wines a 100% produced from a defined grape and originating from a single growing region (relatively small in the exemplary case). In this wine class, wines of the grape "Lagrein" of Laimburg Wine Research Center, 1997 and 1998 vintages, were used.
2. Pure wines, i.e., wines a 100% produced from a single grape and moreover originating from a small growing region. In this wine class, wines of the grape "Cabernet", equally from Laimburg Wine Research Center, 1997 and 1998 vintages, were used.
3. Wines originating from a wide growing region and for whose production a plurality of vines were used. In this wine class a "Chianti Antinori", 1996 vintage, was used, purchased at various retailers in Tyrol and South Tyrol (main constituent is the "Sangiovese" grape).
4. As a quality control for the method of the invention, Majorcan wines were used.

For calibration of the individual class properties, in the exemplary case at least 15 samples each were employed. In the case of calibration for a vintage, 10 samples were used. The number of scans per spectrum and sample was between 3 and 20.

In the 3-D plot of the three principal components (cluster representations), it was possible to represent the wine classes of Lagrein, Sangiovese (Chianti) and Cabernet. Unknown samples could be classified accurately with the aid of the method of the invention.

Moreover with the method of the invention it is possible to discriminate between the 1997 and 1998 vintages in the example of a Cabernet wine, and in unknown samples to state reliably whether and to which one of the exemplarily named vintages they are to be assigned.

In the following, the parameters are indicated whereby the single 3-D plots of FIGS. 1 to 6 were recorded:

FIG. 1 Shows a First Cluster Representation of the Wine Sorts: Chianti and Lagrein, Measured and Evaluated with the Following Parameters:

| | |
|---|---|
| Calibration protocol | Layer thickness: 0.5 mm |
| Software | NIRCAL V3.04 (Build 216) |
| Classes used in calibration set | Chianti, Lagrein (total 2/2) |
| Total number of spectra | 1–81 (total 81/81) |
| No. of calibration spectra | 51/81 |
| No. of validation spectra | total 27/81 |
| Wavelength range [1/cm] | 4008–9996 (total 500/500) |
| Calibration wavelength range [1/cm] | 5628–7404 |
| No. of arithmetic operations for preliminary data processing | 2 |
| Preliminary data processing sequence | 1. Normalization between 0 to 1*, 5628–7404<br>2. Second Derivative Taylor 3 Points |
| Chemometrical method | Cluster |
| No. of primary factors | 5 |
| No. of calibration factors | 1–5 (total 5/5) |

Figure 2:
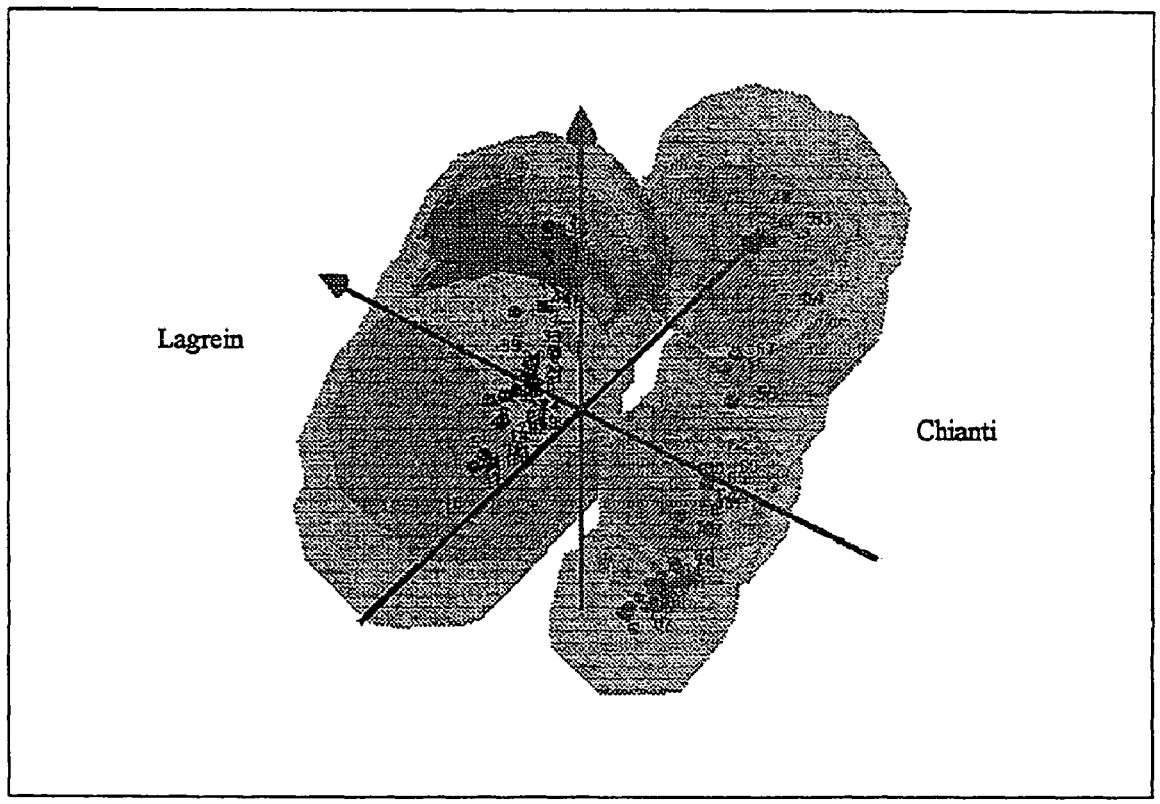
FIG. 2 shows a second cluster representation of the wine sorts: Chianti and Lagrein.

FIG. 2 Shows a second Cluster Representation of the Wine Sorts: Chianti and Lagrein, Measured and Evaluated with the Following Parameters:

| | |
|---|---|
| Calibration protocol | Layer thickness: 3 mm |
| Properties in project | Lagrein, Chianti (total 2/2) |
| Classes used in the calibration set | Lagrein, Chianti (total 2/2) |
| Total number of spectra | 1–91 (total 91/91) |
| No. of calibration spectra | total 51/91 |
| No. of validation spectra | total 40/91 |
| Calibration wavelength range [1/cm] | 4692–9960 |
| No. of arithmetic operations for preliminary data processing | 2 |
| Sequence of preliminary data processing | 1. Normalization between 0 to 1*, 4692–9960<br>2. Second Derivative Taylor 3 Points Cluster |
| Chemometrical method | Cluster |
| No. of primary factors | 4 |
| No. of calibration factors | 1–3 (total 3/4) |

Figure 3:
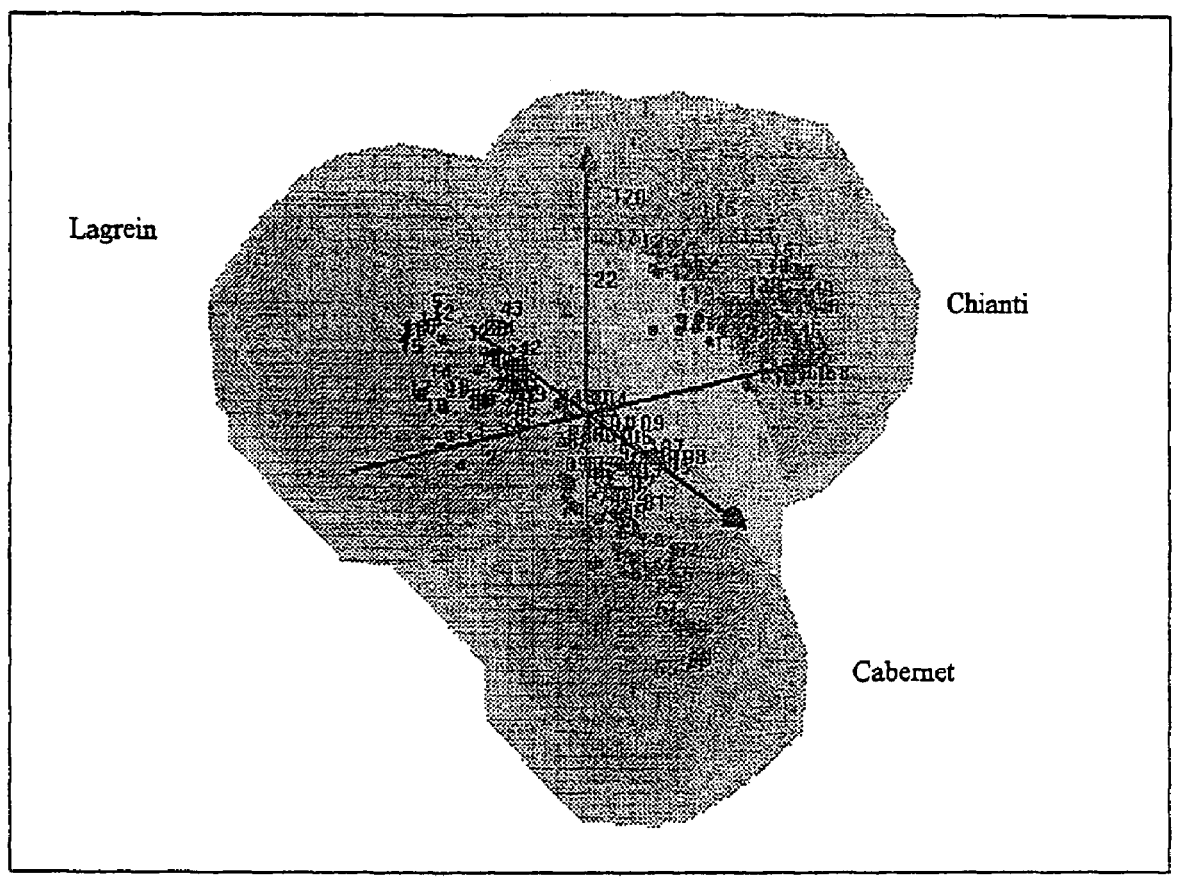
FIG. 3 shows a first cluster representation of the wine sorts: Chianti, Lagrein and Cabernet.

FIG. 3 Shows a First Cluster Representation of the Wine Sorts: Chianti, Lagrein and Cabernet, Measured and Evaluated with the Following Parameters:

| | |
|---|---|
| Calibration Protocol | Layer thickness: 3 mm |
| Total number of spectra | 1–161 (total 161/161) |
| No. of calibration spectra | total 116/161 |
| No. of validation spectra | total 45/161 |
| Wavelength range [1/cm] | 4008–9996 (total 500/500) |
| Calibration wavelength range [1/cm] | 4428–9900 |
| No. of arithmetic operations for preliminary data processing | 2 |
| Sequence of preliminary data processing | 1. Normalization by Maxima*, 4428–9900 (total 457/500)<br>2. Second Derivative Taylor 3 Points |
| Chemometrical method | Cluster |
| No. of primary factors | 6 |
| No. of calibration factors | 1–5 (total 5/6) |

Figure 4:
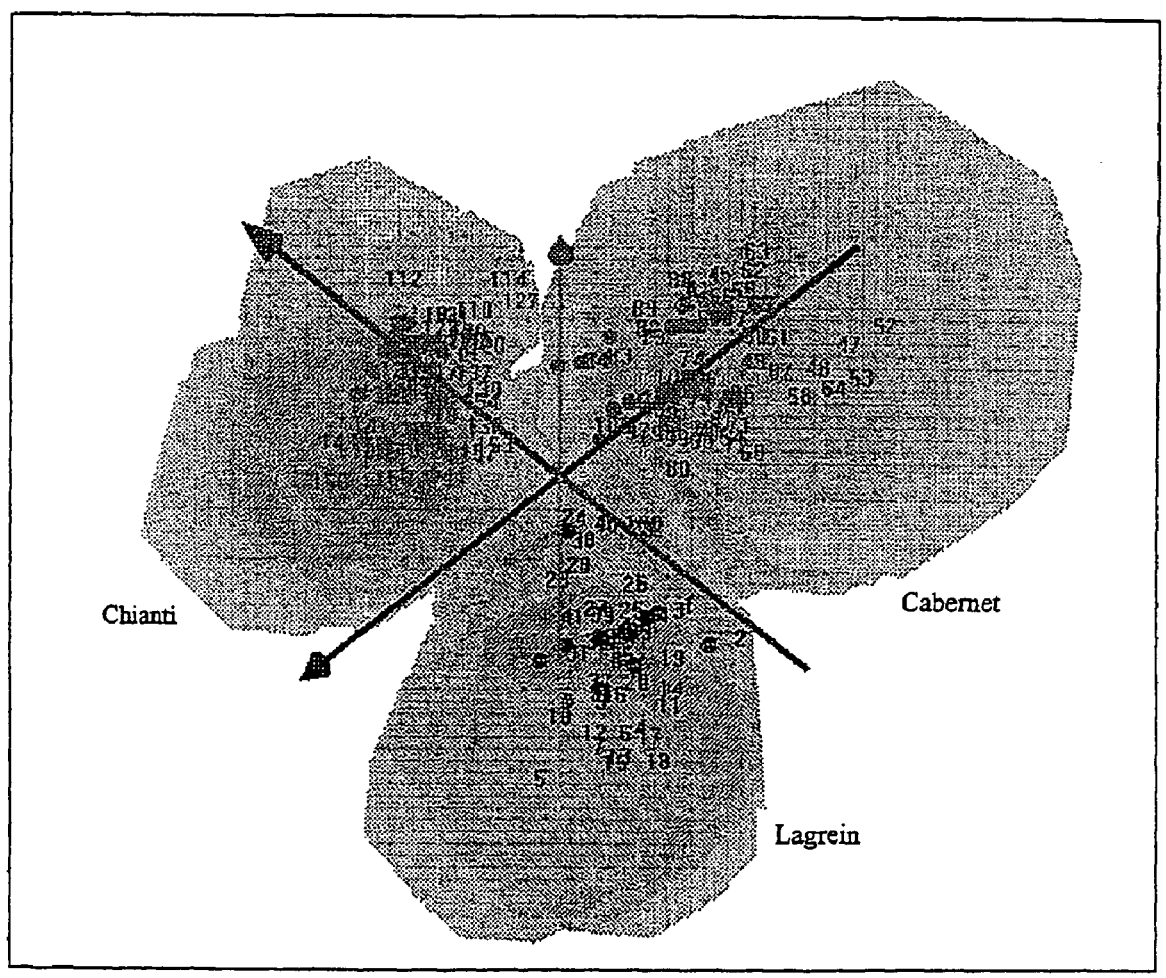
FIG. 4 shows a second cluster representation of the wine sorts: Chianti, Lagrein and Cabernet.

FIG. 4 Shows a Second Cluster Representation of the Wine Sorts: Chianti, Lagrein and Cabernet, Measured and Evaluated with the Following Parameters:

| | |
|---|---|
| Calibration Protocol | Layer thickness: 3 mm |
| Classes used in the calibration set | Lagrein, Cabernet, Chianti (total 3/3) |
| Total number of spectra | 1–157 (total 157/157) |
| No. of calibration spectra | total 116/157 |
| No. of validation spectra | total 41/157 |
| Wavelength range [1/cm] | 4008–9996 (total 500/500) |
| Calibration wavelength range [1/cm] | 4428–9900 |
| No. of arithmetic operations for preliminary data processing | 2 |
| Sequence of preliminary data processing | 1. Smooth Average 3 Points<br>2. Second Derivative Taylor 3 Points |
| Chemometrical method | Cluster |
| No. of primary factors | 4 |
| No. of calibration factors | 1–3 (total 3/4) |

Figure 5:
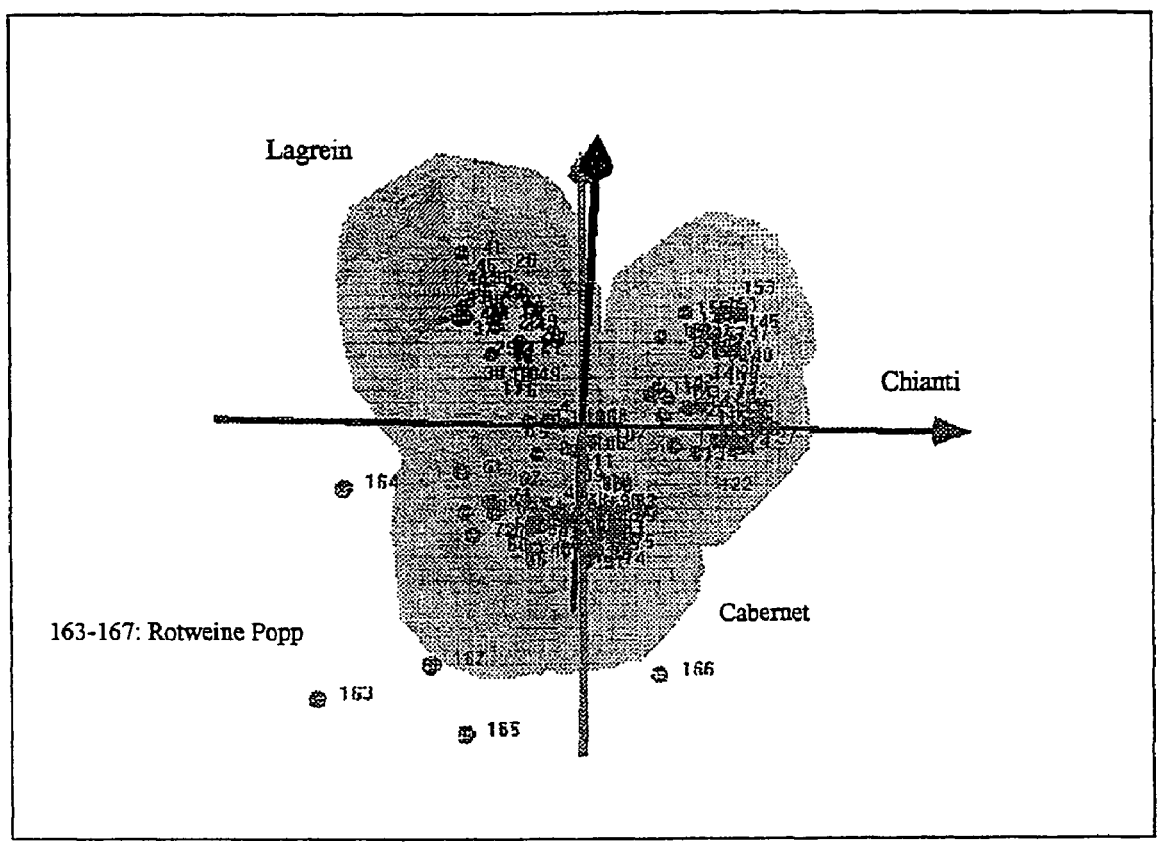
FIG. 5 shows a third cluster representation of the wine sorts: Chianti, Lagrein and Cabernet.

FIG. 5 shows a Third Cluster Representation of the Wine Sorts: Chianti, Lagrein and Cabernet, Measured and Evaluated with the Following Parameters:

| | |
|---|---|
| Calibration Protocol | Layer thickness: 3 mm |
| Classes used in the calibration set | Lagrein, Cabernet, Chianti (total 3/3) |
| No. of calibration spectra | total 119/167 |
| No. of validation spectra | total 48/167 |
| Spectra unused (U-Set) | nothing selected (total 0/167) |
| Wavelength range [1/cm] | 4008–9996 (total 500/500) |
| Calibration wavelength range [1/cm] | 4428–9900 |
| No. of arithmetic operations for preliminary data processing | 2 |
| Sequence of preliminary data processing | 1. Smooth Average 3 Points<br>2. Second Derivative Taylor 3 Points |
| Chemometrical method | Cluster |
| No. of primary factors | 5 |
| No. of calibration factors | 1–5 (total 5/5) |

Figure 6:
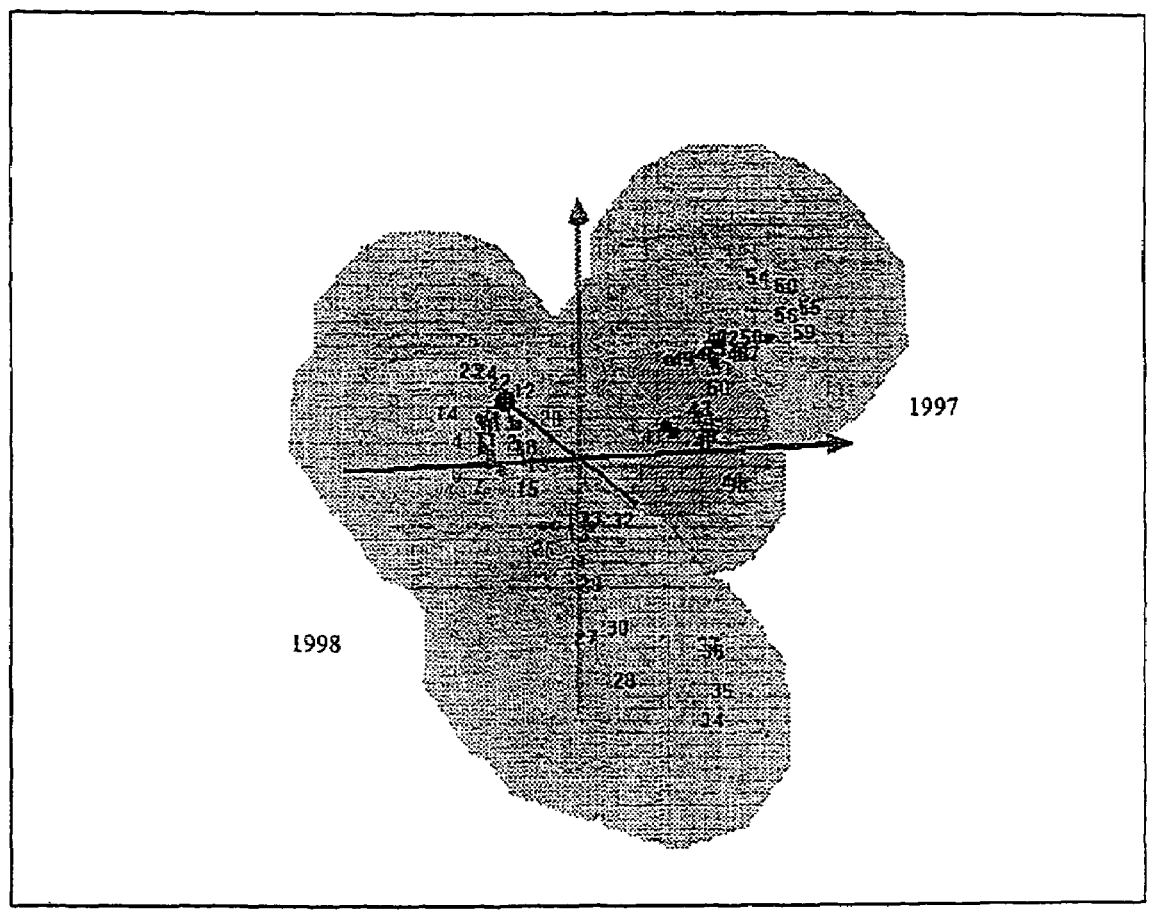
FIG. 6 shows a cluster representation of the Cabernet vintages 1997 and 1998.

FIG. 6 Shows a Cluster Representation of Cabernet Vintages 1997 and 1998, Measured and Evaluated with the Following Parameters:

| | |
|---|---|
| Calibration Protocol | Layer thickness: 3 mm |
| Classes used in the calibration set | 97, 98 (total 2/2) |
| Total number of spectra | 1–60 (total 60/60) |
| No. of calibration spectra | total 45/60 |
| No. of validation spectra | total 15/60 |
| Wavelength range [1/cm] | 4008–9996 (total 500/500) |
| Calibration wavelength range [1/cm] | 4512–9996 |
| No. of arithmetic operations for preliminary data processing | 2 |
| Sequence of preliminary data processing | 1. Smooth Average 3 Points<br>2. Second Derivative Taylor 3 Points |
| Chemometrical method | Cluster |
| No. of primary factors | 3 |
| No. of calibration factors | 1–3 (total 3/3) |

Figure 7:
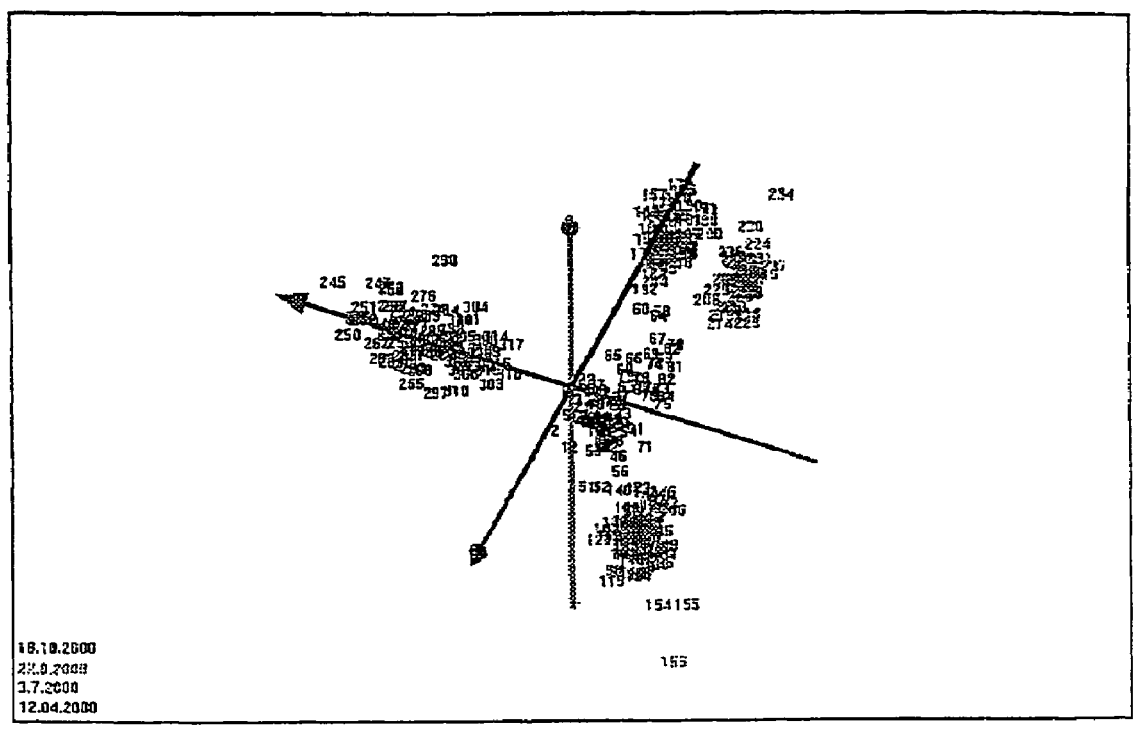
FIG. 7 shows a cluster representation of the maturing process.

FIG. 7 Shows a Cluster Formation of the Maturing Process of Wines of the Tempranillo and Cabernet Sauvignon Grapes, Measured and Evaluated with the Following Parameters:

| | |
|---|---|
| Calibration Protocol | Layer thickness: 3 mm |
| Classes used in the calibration set | 12.04., 3.7., 22.8. and 18.10.2000 (total 4/7) |
| Total number of spectra | Total 213/318 |
| No. of calibration spectra | total 105/318 |
| No. of validation spectra | total 15/60 |
| wavelength range [1/cm] | 4008–9996 (total 500/500) |
| Calibration wavelength range [1/cm] | 4512–9996 |
| No. of arithmetic operations for preliminary data processing | 2 |
| Sequence of preliminary data processing | 1. Normalization between 0 to 1*, 4500–9996 (total 459/500)<br>2. First Derivation Derivative Taylor 3 Punkte |
| Chemometrical method | Cluster |
| No. of primary factors | 8 |
| No. of calibration factors | 1–4 (total 4/8) |

The parameters listed in the above tables—where not self-explanatory—moreover have the following meanings:

Calibration protocol: Layer thickness 0.5 mm: The optical layer thickness used for calibration is 0.5 mm.

Number of arithmetic operations for preliminary data processing: This is the number of mathematical arithmetic operations for preliminary processing of the spectra.

The invention claimed is:

1. A method for classifying beverages of natural origin, comprising the following steps:
   a) providing a plurality of beverage classes, with a plurality of known beverage samples per class, each beverage class having a plurality of known class properties;
   b) irradiating the known beverage samples with irradiated light from a predetermined wavelength range
   c) measuring detected light over a range of wavelengths, the detected light being of at least one of the following types: light passed through the known beverage samples, light reflected from the known beverage samples, light re-emitted from the known beverage samples, or light dispersed by the known beverage samples;
   d) determining a ratio of the irradiated light to the detected light at one or more wavelengths for each known beverage samples of each class, to obtain spectral data;
   e) performing numerical-mathematical conditioning of the spectral data of the individual known beverage samples, to obtain conditioned spectral data;
   f) correlating the conditioned spectral data of a plurality of known beverage samples of each beverage class to one another, to determine a class correlation;
   g) compiling a database from the conditioned spectral data with different beverage classes based on the measured known beverage samples of the individual classes for calibration of a class correlation;
   h) providing at least one unknown beverage sample, said unknown beverage sample having at least partially unknown properties;
   i) irradiating the unknown beverage sample with irradited light from a predetermined wavelength range;
   j) measuring detected light over a range of wavelengths, the detected light being of at least one of the following types: light passed through the unknown beverage samples, light reflected from the unknown beverage samples, light re-emitted from the unknown beverage samples, or light dispersed by the unknown beverage samples;

k) determining a ratio of the irradiated light to the detected light at one or more wavelengths for each unknown beverage sample of each class, to obtain spectral data;

l) performing numerical-mathematical conditioning of the spectral data of the individual unknown beverage samples, to obtain conditioned spectral data;

m) determining the beverage classes to which the unknown beverage sample is to be associated, with the aid of a class correlation of the measured spectra, by using the compiled calibration database of step g), to arrive at a classification result;

n) at least one of representing the classification result to a user, and recording the classification result;

o) repeating steps h-n as necessary to classify additional unknown beverage samples;

wherein correlation of the numerically-mathematically conditioned spectral data is performed by cluster formation.

2. The method according to claim 1, wherein said beverages of natural origin are wines, and wherein the class properties of the individual wine classes comprise properties selected from the group consisting of: type of wine; growing region; grape; vine; vintage; kind of material, including species of wood of the wine cask used for storage/maturing, including American oak, French oak, Hungarian oak, and mixed forms of woods; degree of maturity of storage in cask; chemical parameters, including ethanol content, sugar content, acidity, and 802 content; tannin content; pH value; water content; dry residue; polyphenol content; and toxicological parameters, including glycol content and methanol content.

3. The method according to claim 1, wherein said beverages of natural origin are coffees, and wherein the class properties of the individual beverage classes comprise properties selected from the group consisting of: coffee sort; country of origin; coffee growing region; roasting method; and chemical parameters, including caffeine content, bittering content, acidity, and chlorogenic acids content.

4. The method according to claim 1, wherein the wavelength range of detected light is in the range of approximately 700 to 2,200 nm.

5. The method according to claim 1, wherein a light waveguide is employed for at least one of the following purposes; introduction of the irradiated light to the known beverage samples through the waveguide, measurement of detected light from the known samples through the waveguide, introduction of the irradiated light to the unknown beverage samples through the waveguide, or measurement of detected light from the unknown samples through the waveguide.

6. The method according to claim 1, wherein the thickness of the sample is between about 0.2 and 5 mm.

7. The method according to claim 1, wherein the known beverage samples and the unknown beverage samples are thermostated for measurement.

8. The method according to claim 1, wherein said numerical-mathematical conditioning comprises at least one data reduction selected from the group consisting of normalization, smoothing, 1st derivation, 2nd derivation, multiplicative scatter correction, reciprocal value, square, mean centering, Kubelka Munc transformation, absorption, baseline correction, addition of a constant, and shift negative to zero.

9. The method according to claim 1, wherein said correlation of numerically-mathematically conditioned spectral data comprises at least one multivariate method.

10. The method according to claim 1, wherein the tolerance circles of the individual clusters are adjustable in calibration.

11. The method according to claim 1, wherein approximately 3 to 20 spectral scans per known beverage sample are recorded and wherein approximately 3 to 20 spectral scans per unknown beverage sample are recorded.

12. The method according to claim 1, wherein at least approximately 10 beverage samples per class property are used for calibration.

13. The method according to claim 1, wherein about 70% of all beverage samples measured per class are used for calibration, and about 30% for validation of the method.

14. The method according to claim 1, wherein the classification result is represented on a screen as a 3-D plot.

15. The method according to claim 4, wherein the wavelength range of detected light is in the range of approximately 1,000 to 2,200 nm.

16. The method according to claim 6, wherein the thickness of the sample is between about 0.5 mm and about 3 mm.

17. The method according to claim 7, wherein the known beverage samples and the unknown beverage samples are thermostated for measurement at about 23° C.

18. The method according to claim 9, said at least one multivariate method is selected from the group consisting of a principal components analysis (PCA), a smoothing, a series development, a Taylor series development, an artificial neuronal network algorithm, a backpropagation network, a dynamic learning vector quantization (DLVQ algorithm), a radial basis function (RBF networks), and a RBF networks (RBF-DDA network) trained with a dynamic decay adjustment algorithm (DDA algorithm).

19. The method according to claim 2, wherein the class properties of the individual wine classes comprise properties selected from the group consisting of type of wine; growing region; grape; vine; vintage; kind of material, including species of wood of the wine cask used for storage/maturing, including American oak, French oak, Hungarian oak, and mixed forms of woods; and degree of maturity of storage in cask.

20. The method according to claim 3, wherein the class properties of the individual beverage classes comprise properties selected from the group consisting of coffee sort; country of origin; coffee growing region; and roasting method.

* * * * *